(12) United States Patent
Patel et al.

(10) Patent No.: US 8,852,623 B2
(45) Date of Patent: Oct. 7, 2014

(54) IMPLANTABLE POLYMERIC DEVICE FOR SUSTAINED RELEASE OF DOPAMINE AGONIST

(75) Inventors: Rajesh A. Patel, Redwood City, CA (US); Louis R. Bucalo, Miami, FL (US); Lauren Costantini, San Francisco, CA (US); Sofie Kleppner, Palo Alto, CA (US)

(73) Assignee: Titan Pharmaceuticals, Inc., South San Francisco, CA (US)

(*) Notice: Subject to any disclaimer, the term of this patent is extended or adjusted under 35 U.S.C. 154(b) by 0 days.

(21) Appl. No.: 13/525,193

(22) Filed: Jun. 15, 2012

(65) Prior Publication Data

US 2012/0258161 A1 Oct. 11, 2012

Related U.S. Application Data (60) Continuation of application No. 12/119,334, filed on May 12, 2008, now abandoned, which is a division of application No. 10/815,481, filed on Mar. 31, 2004, now abandoned.

(60) Provisional application No. 60/459,315, filed on Mar. 31, 2003.

(51) Int. Cl.
| | |
|---|---|
| *A61K 9/00* | (2006.01) |
| *A61K 31/48* | (2006.01) |
| *A61K 9/16* | (2006.01) |
| *A61L 31/16* | (2006.01) |
| *A61K 31/485* | (2006.01) |
| *A61K 31/381* | (2006.01) |
| *A61K 31/428* | (2006.01) |
| *A61K 31/4045* | (2006.01) |
| *A61K 9/14* | (2006.01) |
| *A61L 31/04* | (2006.01) |

(52) U.S. Cl.
CPC ............ *A61K 9/0024* (2013.01); *A61K 31/48* (2013.01); *A61L 2300/20* (2013.01); *A61L 2300/41* (2013.01); *A61K 9/1635* (2013.01); *A61L 31/16* (2013.01); *A61K 31/485* (2013.01); *A61K 31/381* (2013.01); *A61K 31/428* (2013.01); *A61K 31/4045* (2013.01); *A61L 2300/40* (2013.01); *A61K 9/146* (2013.01); *A61L 31/048* (2013.01)
USPC ....................................................... 424/423

(58) Field of Classification Search
CPC .................................................. A61K 9/0024
USPC ............................................................ 424/423
See application file for complete search history.

(56) References Cited

U.S. PATENT DOCUMENTS

| | | | |
|---|---|---|---|
| 3,689,634 A | 9/1972 | Kliment et al. | |
| 3,717,639 A | 2/1973 | Neumeyer | |
| 3,814,768 A | 6/1974 | Fishman | |
| 3,923,939 A * | 12/1975 | Baker et al. | 264/49 |
| 4,069,307 A | 1/1978 | Higuchi et al. | |
| 4,148,871 A | 4/1979 | Pitt et al. | |
| 4,351,337 A | 9/1982 | Sidman | |
| 4,450,150 A | 5/1984 | Sidman | |
| 4,464,378 A | 8/1984 | Hussain | |
| 4,535,157 A | 8/1985 | Meltzer et al. | |
| 4,543,256 A | 9/1985 | Neumeyer | |
| 4,582,835 A | 4/1986 | Lewis et al. | |
| 4,599,342 A | 7/1986 | LaHann | |
| 4,622,219 A | 11/1986 | Haynes | |
| 4,661,492 A | 4/1987 | Lewis et al. | |
| 4,670,014 A | 6/1987 | Huc et al. | |
| 4,678,809 A | 7/1987 | Phillips | |
| 4,692,451 A | 9/1987 | Dodman et al. | |
| 4,725,442 A | 2/1988 | Haynes | |
| 4,818,542 A | 4/1989 | DeLuca et al. | |
| 4,861,627 A | 8/1989 | Mathiowitz et al. | |
| 4,882,335 A | 11/1989 | Sinclair | |
| 4,883,666 A | 11/1989 | Sabel et al. | |
| 4,897,268 A | 1/1990 | Tice et al. | |
| 4,898,733 A | 2/1990 | DePrince et al. | |
| 4,935,428 A | 6/1990 | Lewis | |
| 4,957,119 A | 9/1990 | de Nijs | |
| 4,962,091 A | 10/1990 | Eppstein et al. | |
| 4,983,586 A | 1/1991 | Bodor | |

(Continued)

FOREIGN PATENT DOCUMENTS

| | | |
|---|---|---|
| EP | 0 069 600 A2 | 1/1983 |
| EP | 0 069 600 A3 | 1/1983 |
| EP | 0 153 896 A2 | 9/1985 |
| EP | 0 153 896 A3 | 9/1985 |
| EP | 0 153 896 B1 | 9/1985 |

(Continued)

OTHER PUBLICATIONS

Anonymous (Date Unknown). "NSAIDs Traditional NSAIDs," located at <http:www.arthritis.org/conditions/DrugGuide/Chart_nsaids.asp>, last visited on Mar. 27, 2003, 4 pages.

(Continued)

*Primary Examiner* — Jake Vu
(74) *Attorney, Agent, or Firm* — Morrison & Foerster LLP (57) ABSTRACT

The present invention provides compositions, methods, and kits for treatment of Parkinson's disease and other conditions for which treatment with a dopamine agonist is therapeutically beneficial. The invention provides a biocompatible non-erodible polymeric device which releases dopamine agonist continuously with generally linear release kinetics for extended periods of time. Dopamine agonist is released through pores that open to the surface of the polymeric matrix in which it is encapsulated. The device may be administered subcutaneously to an individual in need of continuous treatment with dopamine agonist.

75 Claims, 2 Drawing Sheets

(56) References Cited

U.S. PATENT DOCUMENTS

| | | | |
|---|---|---|---|
| 4,994,281 A | 2/1991 | Muranishi et al. | |
| 5,024,998 A | 6/1991 | Bodor | |
| 5,069,909 A | 12/1991 | Sharma et al. | |
| 5,075,341 A | 12/1991 | Mendelson et al. | |
| 5,086,058 A | 2/1992 | Sinclair et al. | |
| 5,114,718 A | 5/1992 | Damani | |
| 5,114,719 A | 5/1992 | Sabel et al. | |
| 5,128,145 A | 7/1992 | Edgren et al. | |
| 5,156,844 A | 10/1992 | Aebisher et al. | |
| 5,211,951 A | 5/1993 | Sparer et al. | |
| 5,219,858 A | 6/1993 | Parnell | |
| 5,236,714 A | 8/1993 | Lee et al. | |
| 5,240,711 A | 8/1993 | Hille et al. | |
| 5,298,017 A | 3/1994 | Theeuwes et al. | |
| 5,478,577 A | 12/1995 | Sackler et al. | |
| 5,486,362 A | 1/1996 | Kitchell et al. | |
| 5,562,917 A | 10/1996 | Durif et al. | |
| 5,565,443 A | 10/1996 | Lanquetin et al. | |
| 5,574,052 A | 11/1996 | Rose et al. | |
| 5,580,578 A | 12/1996 | Oshlack et al. | |
| 5,580,876 A | 12/1996 | Crain et al. | |
| 5,585,460 A | 12/1996 | Yamada et al. | |
| 5,587,381 A | 12/1996 | Sinclair | |
| 5,601,835 A | 2/1997 | Sabel et al. | |
| 5,604,198 A | 2/1997 | Poduslo et al. | |
| 5,618,553 A | 4/1997 | Kelleher | |
| 5,618,555 A | 4/1997 | Tokuda et al. | |
| 5,633,000 A * | 5/1997 | Grossman et al. | 424/422 |
| 5,650,173 A | 7/1997 | Ramstack et al. | |
| 5,651,986 A | 7/1997 | Brem et al. | |
| 5,654,008 A | 8/1997 | Herbert et al. | |
| 5,703,101 A | 12/1997 | Rose et al. | |
| 5,718,921 A | 2/1998 | Mathiowitz et al. | |
| 5,726,190 A | 3/1998 | Rose et al. | |
| 5,732,717 A | 3/1998 | Watanabe et al. | |
| 5,750,136 A | 5/1998 | Scholz et al. | |
| 5,756,483 A | 5/1998 | Merkus | |
| 5,770,231 A | 6/1998 | Mesens et al. | |
| 5,770,606 A | 6/1998 | El-Rashidy et al. | |
| 5,840,719 A | 11/1998 | Rubin et al. | |
| 5,851,547 A | 12/1998 | Fujioka et al. | |
| 5,858,388 A | 1/1999 | Grossman et al. | |
| 5,877,224 A | 3/1999 | Brocchini et al. | |
| 5,919,473 A | 7/1999 | Elkhoury | |
| 5,935,975 A | 8/1999 | Rose et al. | |
| 5,939,094 A | 8/1999 | Durif et al. | |
| 5,965,168 A | 10/1999 | Mesens et al. | |
| 5,968,547 A | 10/1999 | Reder et al. | |
| 5,968,551 A | 10/1999 | Oshlack et al. | |
| 5,980,927 A | 11/1999 | Nelson et al. | |
| 5,980,948 A | 11/1999 | Goedemoed et al. | |
| 5,994,363 A | 11/1999 | El-Rashidy et al. | |
| 6,001,845 A | 12/1999 | Estok | |
| 6,004,962 A | 12/1999 | Gooberman | |
| 6,004,969 A | 12/1999 | Hu et al. | |
| 6,007,841 A | 12/1999 | Caruso | |
| 6,011,043 A | 1/2000 | Estok | |
| 6,117,454 A | 9/2000 | Kreuter et al. | |
| 6,126,956 A | 10/2000 | Grossman et al. | |
| 6,136,818 A | 10/2000 | Estok | |
| 6,203,813 B1 | 3/2001 | Gooberman | |
| 6,228,863 B1 | 5/2001 | Palermo et al. | |
| 6,271,240 B1 | 8/2001 | Simon | |
| 6,342,250 B1 | 1/2002 | Masters | |
| 6,344,212 B2 | 2/2002 | Reder et al. | |
| 6,461,485 B2 | 10/2002 | Mizouchi et al. | |
| 6,495,155 B1 | 12/2002 | Tice et al. | |
| 6,512,009 B1 | 1/2003 | Daoust et al. | |
| 6,541,021 B1 | 4/2003 | Johnson et al. | |
| 6,613,358 B2 | 9/2003 | Randolph et al. | |
| 6,919,330 B2 * | 7/2005 | Vaddadi | 514/220 |
| 7,270,830 B2 | 9/2007 | Reidenberg et al. | |
| 7,736,665 B2 | 6/2010 | Patel et al. | |

| | | |
|---|---|---|
| 2001/0036469 A1 | 11/2001 | Gooberman |
| 2002/0034534 A1 | 3/2002 | Barr et al. |
| 2002/0049232 A1 | 4/2002 | Svensson |
| 2002/0198574 A1 | 12/2002 | Gumpert |
| 2003/0039689 A1 | 2/2003 | Chen et al. |
| 2003/0211157 A1 | 11/2003 | Simon |
| 2004/0009222 A1 | 1/2004 | Chou et al. |
| 2004/0024006 A1 | 2/2004 | Simon |
| 2004/0033250 A1 | 2/2004 | Patel et al. |
| 2005/0031667 A1 | 2/2005 | Patel et al. |
| 2005/0031668 A1 | 2/2005 | Patel et al. |
| 2005/0245541 A1 | 11/2005 | Ehrich et al. |
| 2007/0275031 A1 | 11/2007 | Patel et al. |
| 2008/0026031 A1 | 1/2008 | Patel et al. |
| 2008/0311171 A1 | 12/2008 | Patel et al. |
| 2009/0162412 A1 | 6/2009 | Patel et al. |
| 2013/0171229 A1 | 7/2013 | Patel et al. |

FOREIGN PATENT DOCUMENTS

| | | |
|---|---|---|
| EP | 0 226 061 A2 | 6/1987 |
| EP | 0 226 061 A3 | 6/1987 |
| EP | 0 226 061 B1 | 6/1987 |
| EP | 0 478 671 B1 | 4/1992 |
| EP | 0 531 415 B1 | 3/1993 |
| EP | 0 945 133 A1 | 9/1999 |
| GB | 2 136 688 A | 9/1984 |
| JP | 3-193732 A | 8/1991 |
| JP | 5-500620 A | 2/1993 |
| JP | 8-506318 A | 7/1996 |
| JP | 11-501306 A | 2/1999 |
| JP | 2000-505419 T | 5/2000 |
| JP | 2000-513736 A | 10/2000 |
| JP | 2002-513752 A | 5/2002 |
| WO | WO-89/05632 A1 | 6/1989 |
| WO | WO-90/15637 A2 | 12/1990 |
| WO | WO-91/18605 A1 | 12/1991 |
| WO | WO-94/06437 A1 | 3/1994 |
| WO | WO-96/00537 A1 | 1/1996 |
| WO | WO-96/26738 A1 | 9/1996 |
| WO | WO-97/30656 A1 | 8/1997 |
| WO | WO-98/20684 A2 | 5/1998 |
| WO | WO-98/31368 A1 | 7/1998 |
| WO | WO-99/56731 A1 | 11/1999 |
| WO | WO-00/19976 A2 | 4/2000 |
| WO | WO-00/19976 A3 | 4/2000 |
| WO | WO-00/35456 A1 | 6/2000 |
| WO | WO-00/72827 A2 | 12/2000 |
| WO | WO-00/72827 A3 | 12/2000 |
| WO | WO-01/10455 A1 | 2/2001 |
| WO | WO-02/056745 A2 | 7/2002 |
| WO | WO-03/101358 A1 | 12/2003 |
| WO | WO-2004/089375 A1 | 10/2004 |
| WO | WO-2007/139744 A2 | 12/2007 |

OTHER PUBLICATIONS

Anonymous. (Jul. 2001). "Buprenex®," NDC 12496-0757-1, 2 pages.

Anonymous (May 14, 2002). "Titan Reports First Quarter 2002 Results," located at <http://www.accessmylibrary.com/coms2/summary_0286-25350537_ITM>, last visited on May 29, 2008, 5 pages.

Anonymous (Jun. 7, 2002). "Titan Announces Probuphine Demonstrates Continuous Delivery of Buprenorphine for Eight Months in Preclinical Studies; Novel Long-Term Delivery System for Treatment of Addiction," located at <http://www.accessmylibrary.com/coms2/summary_0286-25427865_ITM>, last visited on May 29, 2008, 3 pages.

Anonymous (Dec. 14, 2002). "India Infoline Sector Reports Pharmaceuticals," located at <http:www.inidainfoline.com/sect/phfo/ch21.html>, last visited Mar. 27, 2003, 2 pages.

Bibbiani, F. et al. (2005, e-published on Jan. 19, 2005). "Continuous Dopaminergic Stimulation Reduces Risk of Motor Complications in Parkinsonian Primates," *Experimental Neurology* 192:73-78.

(56) References Cited

OTHER PUBLICATIONS

Bibbiani, F. et al. (Date Unknown). "Continuous Apomorphine Administration with Novel EVA Implants Reduces the Risks of Motor Compilations Compared to Pulsatile Aporphormine in L-DOPA-Naïve, MPTP-Lesioned Primates," Abstract Preview: AAN3L_1225, located at <http://www.abstracts-on-line.com>, last visited on Feb. 6, 2003, 1 page.

Bibbiani, F. et al. (Mar. 2003). "Continuous Apomorphine Administration with Novel EVA Implants Reduces the Risks of Motor Compilations Compared to Pulsatile Aporphormine in L-DOPA-Naive, MPTP-Lesioned Primates," Abstract, presented at the Core 55th Annual Meeting Program, Honolulu, HI, Mar. 29-Apr. 5, 2003, *Neurology* 60(5)(Suppl. 1):A330:Abstract No. S39.001, 3 pages.

Bullingham, R.E.S. et al. (Nov. 1980). "Buprenorphine Kinetics," *Clinical Pharmacology and Therapeutics* 28(5):667-672.

Bullingham, R.E.S. et al. (1981). "Sublingual Buprenorphine Used Postoperatively: Clinical Observations and Preliminary Pharmacokinetic Analysis," *Br. J. Clin. Pharmac.* 12:117-122.

Bye, A. et al. (Nov. 2008). "Pharmacokinetic Analyses in Subjects Treated for 6 Months with Buprenorphine Implants," *International Society of Addiction Medicine*, Nov. 16-20, 2008, Cape Town, South Africa, 14 pages.

Casadonte, P. P. et al. (Nov., 2008). "Phase 3 Results Evaluating the Safety and Efficacy of a 6-month, Sustained Release, Implantable Formulation of Buprenorphine, (Probuphine®)," *International Society of Addiction Medicine*, Nov. 16-20, 2008, Cape Town, South Africa, 25 pages.

Cassidy, J.P. et al. (1993). "Controlled Buccal Delivery of Buprenorphine," *J. Controlled Release* 25:21-29.

Castaño, A. et al. (2002). "The Degenerative Effect of a Single Intranigral Injection of LPS on the Dopaminergic System is Prevented by Dexamethasone, and not Mimicked by rh-TNF-α, IL-1β and IFN-γ," *Journal of Neurochemistry* 81:150-157.

Chow, B.L.C. et al. (1997). "Effect of Naltrexone and Its Derivatives, Nalmefene and Naltrindole, on Conditioned Anticipatory Behaviour and Saccharin Intake in Rats," *Behavioural Pharmacology* 8(8):725-735.

Cowan, A. et al. (1977). "Agonist and Antagonist Properties of Buprenorphine, a New Antinociceptive Agent," *Br. J. Pharmac.* 60:537-545.

Cowan, A. et al. (1977). "The Animal Pharmacology of Buprenorphine, an Oripavine Analgesic Agent," *Br. J. Pharmac.* 60:547-554.

Croop, R.S. et al. (Dec. 1997). "The Safety Profile of Naltrexone in the Treatment of Alcoholism," *Arch. Gen. Psychiatry* 54:1130-1135.

Dixon, R. et al. (Jan. 1986). "Nalmefene: Intravenous Safety and Kinetics of a New Opioid Antagonist," *Clin. Pharmacol. Ther.* 39(1):49-53.

Dupont (Date Unknown). "Elvax® Specialty EVA Resins," located at <http://www2.dupont.com/Elvax/en_US/products/eva_resins.html>, last visited on Nov. 19, 2007, 7 pages.

During, M.J. et al. (Apr. 1989). "Controlled Release of Dopamine from a Polymeric Brain Implant: in Vivo Characterization," *Ann. Neurol.* 25(4):351-356.

European Examination Communication mailed on Aug. 29, 2008, for European Patent Application No. 04753725.3, filed on May 27, 2004, 3 pages.

European Search Report mailed on Dec. 1, 2009, for European Patent Application No. 03731501.7, filed on Dec. 17, 2004, 3 pages.

Extended European Search Report mailed on Jan. 21, 2013 for European Patent Application No. 12193435.0, filed on Jun. 2, 2003, 10 pages.

Evans, H.C. et al. (2003). "Transdermal Buprenorphine," *Drugs* 63(19):1999-2010.

Freese, A. et al. (1989). "Controlled Release of Dopamine from a Polymeric Brain Implant: in Vitro Characterization," *Exp. Neurol.* 103:234-238.

Fudala, P. J. et al. (Mar. 1991). "Human Pharmacology and Abuse Potential of Nalmefene," *Clin. Pharmacol. Ther.* 49(3):300-306.

Fuller, R.K. et al. (Sep. 19, 1986). "Disulfiram Treatment of Alcoholism: A Veterans Administration Cooperative Study," *JAMA* 256(11):1449-1455.

Greenwald, M. et al. (2007). "Buprenorphine Duration of Action: Mu-opioid Receptor Availability and Pharmacokinetic and Behavioral Indices," *Biol. Psychiatry* 61:101-110.

Greenwald, M.K. et al. (2003, e-pub. Aug. 6, 2003). "Effects of Buprenorphine Maintenance Dose on µ-Opioid Receptor Availability, Plasma Concentrations, and Antagonist Blockade in Heroin-Dependent Volunteers," *Neuropsychopharmacology* 28:2000-2009.

Gueye, P.N. et al. (2001). "Lack of Effect of Single High Doses of Buprenorphine on Arterial Blood Gases in the Rat," *Toxicological Sciences* 62:148-154.

Haik-Creguer, K.L. et al. (1998). "Small Drug Sample Fabrication of Controlled Release Polymers Using the Microextrusion Method," *Journal of Neuroscience Methods* 80:37-40.

Hamilton, R.J. et al. (Jan. 2002). "Complications of Ultrarapid Opioid Detoxification with Subcutaneous Naltrexone Pellets," *Acad. Emergency Medicine* 9(1):63-68.

Hardman, J.G. et al., eds. (2001). "Dopamine-Receptor Agonists," in *Goodman & Gilman's the Pharmacological Basis of Therapeutics*, Tenth Edition, McGraw-Hill: New York, NY, pp. 557-558.

Hardman, J.G. et al., eds. (2001). "Levodopa," in *Goodman & Gilman's the Pharmacological Basis of Therapeutics*, Tenth Edition, McGraw-Hill: New York, NY, pp. 555-557.

Herrmann, S. (2007). Thesis Dissertation, *Lipidic Implants for Pharmaceutical Proteins: Mechanisims of Release and Development of Extruded Devices*, Ludwig-Maximilians-University Munich, 222 pages.

Hill, H.F. et al. (Feb. 15, 1991). "Clinical Trials: Patient-Controlled Analgesic Administration. A Comparison of Steady-State Morphine Infusions with Bolus Doses," *Cancer* 67(4):874-882.

Hubbell, C.L. et al. (1991). "Opioidergic, Serotonergic, and Dopaminergic Manipulations and Rats' Intake of a Sweetened Alcoholic Beverage," *Alcohol* 8:355-367.

International Search Report mailed on Aug. 20, 2003, for PCT Application No. PCT/US03/17401, filed on Jun. 2, 2003, 1 page.

International Search Report mailed on Sep. 13, 2004 for PCT Application No. PCT/US2004/010270, filed on Mar. 31, 2004, 5 pages.

International Search Report mailed Dec. 21, 2004 for PCT patent Application No. PCT/US2004/016944 filed on May 27, 2004, 6 pages.

International Search Report mailed on Sep. 18, 2008, for PCT Application No. PCT/US2007/012046, filed May 18, 2007, 8 pages. (39.40).

Johnsen, J. et al. (May-Jun. 1991). "Disulfiram Implant: A Double-Blind Placebo Controlled Follow-Up on Treatment Outcome," *Alcohol Clin. and Exp. Res.* 15(3):532-536.

Johnsen, J. et al. (1987). "A Double-blind Placebo Controlled Study of Male Alcoholics Given a Subcutaneous Disulfiram Implantation," *British Journal of Addiction* 82(6):607-613.

Johnson, R.E. et al. (May 27, 1992). "A Controlled Trial of Buprenorphine Treatment for Opioid Dependence," *JAMA* 267(20):2750-2755.

June, H.L. et al. (Dec. 1998). "The Opioid Receptor Antagonist Nalmefene Reduces Responding Maintained by Ethanol Presentation: Preclinical Studies in Ethanol-Preferring and Outbred Wistar Rats," *Alcohol Clin. Exp. Res.* 22(9):2174-2185.

Kalachandra, S. et al. (2002). "Controlled Drug Release for Oral Condition by a Novel Device Based on Ethylene Vinyl Acetate (EVA)," *Journal of Materials Science: Materials in Medicine* 13:53-58.

Kamei, S. et al. (1996). "Influence of Low-Molecular Weight Fraction of Polymer on Entrapment and Initial Release of Leuprorelin," *Proc. Int. Symp. Control. Rel. Bioact Mater.* 23:347-348.

Kay, D.C. et al. (1981). "Morphine-Like Insomnia from Heroin in Nondependent Human Addicts," *British Journal of Clinical Pharmacology* 11:159-169.

Kuhlman, Jr., J.J., et al. (1998). "Relationship of Plasma Buprenorphine and Norbuprenorphine to Withdrawal Symptoms During Dose Induction, Maintenance and Withdrawal from Sublingual Buprenorphine," *Addiction* 93(4):549-559.

(56) References Cited

OTHER PUBLICATIONS

Kuhlman, Jr., J.J. et al. (Oct. 1996). "Human Pharmacokinetics of Intravenous, Sublingual, and Buccal Buprenorphine," *Journal of Analytical Toxicology* 20(6):369-378.

Kuhlman, Jr., J.J. (1996). "An Investigation of Buprenorphine and Norbuprenorphine Plasma Concentrations in Opioid Dependence Therapy: Analysis, Pharmacokinetics and Chronic Administration," A Dissertation submitted to the Faculty of the Graduate School of the University of Maryland in partial fulfillment of the requirements for the degree of Doctor of Philosophy, 140 pages.

Lamprecht, A. et al. (2001). "Biodegradable Nanoparticles for Targeted Drug Delivery in Treatment of Inflammatory Bowel Disease," *The Journal of Pharmacology and Experimental Therapeutics* 299(2):775-781.

Lehmann, K.A. (1984). "On-Demand Analgesie: Neue Möglichkeiten zur Behandlung acuter Schmerzen [on Demand Analgesia: New Concepts for Treatment of Acute Pain]," *Arzneimittelforschung* 34(9A):1108-1114, (Translation of Abstract Only.).

Lesser, G.L. et al. (May/Jun. 1996). "In Vitro and in Vivo Studies of Subcutaneous Hydromorphone Implants Designed for the Treatment of Cancer Pain," *Pain* 65(2,3):265-272.

Ling, W. et al. (May 1996). "A Controlled Trial Comparing Buprenorphine and Methadone Maintenance in Opioid Dependence," *Arch. Gen. Psychiatry* 53(5):401-407.

Ling, W. (1998). "Buprenorphine Maintenance Treatment of Opiate Dependence: A Multicenter, Randomized Clinical Trial," *Addiction* 93(4):475-486.

Malinoff, H.L. et al. (2005). "Sublingual Buprenorphine is Effective in the Treatment of Chronic Pain Syndrome," *American Journal of Therapeutics* 12(5):379-384.

Martin, W.R. et al. (1976). "The Effects of Morphine- and Nalorphine-like Drugs in the Nondependent and Morphine-Dependent Chronic Spinal Dog," *J. Pharmacol. Exp. Ther.* 197(3):517-532.

Mason, B.J. et al. (Aug. 1999). "A Double-blind, Placebo-Controlled Study of Oral Nalmefene for Alcohol Dependence," *Arch. Gen. Psychiatry* 56(8):719-724.

Mason, B.J. et al. (Sep./Oct. 1994). "A Double-Blind, Placebo-Controlled Pilot Study to Evaluate the Efficacy and Safety of Oral Nalmefene HCl for Alcohol Dependence," *Alcohol Clin. Exp. Res.* 18(5):1162-1167.

McAleer, S.D. et al. (Oct. 24, 2003). "Pharmacokinetics of High Dose Buprenorphine Following Single Administration of Sublingual Tablet Formulations in Opiod Naive Healthy Male Volunteers under a Naltrexone Block," *Drug and Alcohol Dependence* 72(1):75-83.

McQuinn, R.L. et al. (1995). "Sustained Oral Mucosal Delivery in Human Volunteers of Buprenorphine from a Thin Non-Eroding Mucoadhesive Polymeric Disk," *Journal of Controlled Release* 34:243-250.

Medical Economics—Staff, eds. (2002). "Buprenex®," *Physicans' Desk Reference* 2002, 56th Edition, Medical Economic Company, Inc.: Montvale, NJ, pp. 2918-2919.

Medical Economics—Staff, eds. (2003). "Buprenex®," *Physicans' Desk Reference* 2003, 57th Edition, Medical Economic Company, Inc.: Montvale, NJ, pp. 2857-2859.

Medical Economics—Staff, eds. (2004). "Buprenex®," *Physicans' Desk Reference* 2004, 58th Edition, Medical Economic Company, Inc.: Montvale, NJ, Brand and Generic Name Index p. 123, Product Identification Guide p. 333, pp. 2866-2869.

Mehta, M., ed. (1997). *PDR Guide to Drug Interactions Side Effects Indications Contraindications*, 51st edition, Medical Economics Company, Inc.: New Jersey, pp. 957-959 (Interactions Index only).

Mendelson, J.H. et al. (Apr. 1989). "Naloxone Suppresses Buprenorphine Stimulation of Plasma Prolactin," *Journal of Clinical Psychopharmacology* 9(2):105-109.

Michel, M.E. et al. (1985). "Binding of a New Opiate Antagonist, Nalmefene, to Rat Brain Membranes," *Meth. and Find Exptl. Clin Pharmacol.* 7(4):175-177.

Misra, A.L. et al. (1980). "An Improved Long-Acting Delivery System for Narcotic Antagonists," *NIDA Res. Monograph* 28:254-264.

Nath, R.P. et al. (1999). "Buprenorphine Pharmacokinetics: Relative Bioavailability of Sublingual Tablet and Liquid Formulations," *J. Clin. Pharmacol.* 39:619-623.

Ohtani, M. et al. (Feb. 1995). "Comparative Analysis of Buprenorphine-and Norbuprenorphine-Induced Analgesic Effects Based on Pharmacokinetic-Pharmacodynamic Modeling," *Journal of Pharmacology and Experimental Therapeutics* 272(2):505-510.

O'Malley, S.S. et al. (Mar. 1996). "Six-Month Follow-up of Naltrexone and Psychotherapy for Alcohol Dependence," *Arch. Gen. Psychiatry* 53(3):217-224.

O'Malley, S.S. et al. (Nov. 1992). "Naltrexone and Coping Skills Therapy for Alcohol Dependence: A Controlled Study," *Arch. Gen. Psychiatry* 49(11):881-887.

Oertel, W.H. et al. (1995)."Special Article. International Guide to Drugs for Parkinson's Disease," *Movement Disorders* 10(2):121-131.

Oslin, D. et al. (1997). "Naltrexone as an Adjunctive Treatment for Older Patients With Alcohol Dependence," *The American Journal of Geriatric Psychiatry* 5(4):324-332.

Patel, R.A. (2002). "Long Term Delivery of Buprenorphine by an Implantable Delivery System," presented at the International Conference on Pain and Chemical Dependency, New York, NY, Jun. 6-8, 2002, 1 page.

Patel, R. (2001). "Buprenorphine Implants: Novel Treatment for Opiate Dependence," Poster Presentation: Pharmaceutical Congress of the Americas: Orlando, Fl, Mar. 24-29, 2001, three pages.

Pontani, R.B. et al. (Mar. 1, 1983). "A Long-Acting Buprenorphine Delivery System," *Pharmacology Biochemistry and Behavior* 18(3):471-474.

Raasch, W. et al. (2000). "In Vitro and in Vivo Long Term Release of Apomorphine from Polymer Matrices," *Jpn. J. Pharmacol.* 84:36-43.

Rhine, W.D. et al. (Mar. 1980). "Polymers for Sustained Macromolecule Release Procedures to Fabricate Reproducible Delivery Systems and Control Release Kinetics," *Journal of Pharmaceutical Sciences* 69(3):265-270.

Sabel, B.A. (1990). "Extended Levodopa Release from Subcutaneously Implanted Polymer Matrix in Rats," *Annals of Neurology* 28(5):714-717.

Schuh, K.J. et al. (1999). "Pharmacokinetic Comparison of the Buprenorphine Sublingual Liquid and Tablet," *Drug Alcohol Depend.* 56:55-60.

Schwope, A.D. et al. (1975). "Development of Polyactic/Glycolic Acid Delivery Systems for Use in Treatment of Narcotic Addiction," *NIDA Res. Monograph Series* 4:13-18.

Shippenberg, T.S. et al. (2002). "Recent Advances in Animal Models of Drug Addiction: Definitions and Validation of Animal Models," Chapter 97 in *Neuropsychopharmacology: The Fifth Generation of Progress*, Davis, K.I. et al. eds., Lippincott Williams & Wilkins, Philadelphia, PA, pp. 1381-1397.

Shuwisitkul, D. (May 2011). Inaugural-Dissertation, *Biodegradable Implants With Different Drug Release Profiles*, Freie Universität Berlin, 166 pages.

Skingle, M. et al. (1980). "Further Studies on Opiate Receptors That Mediate Antinoception: Tooth Pulp Stimulation in the Dog," *Br. J. Pharmac.*, 70:323-327.

Sobel, B-F.X. et al. (Jan. 7, 2004). "Open-Label Trial of an Injection Depot Formulation of Buprenorphine in Opioid Detoxification," *Drug and Alcohol Dependence* 73(1):11-22.

Strain, E.C. et al. (2004). "Relative Bioavailability of Different Buprenorphine Formulations Under Chronic Dosing Conditions," *Drug and Alcohol Dependence* 74:37-43.

Tabakoff, B. et al. (1983). "Alcohol Interactions with Brain Opiate Recceptors," *Life Sciences* 32:197-204.

Tigerstedt, I. et al. (1980). "Double-blind, Multiple-dose Comparison of Buprenorphine and Morphine in Postoperative Pain," *Acta Anaesthesiologica Scandanavia* 24:462-468.

Volpicelli, J.R. et al. (Aug. 1997). "Naltrexone and Alcohol Dependence: Role of Subject Compliance," *Arch. Gen. Psychiatry* 54:737-742.

Volipcelli, J.R. et al. (Nov. 1992). "Naltrexone in the Treatment of Alcohol Dependence," *Arch. Gen. Psychiatry* 49:876-880.

(56) References Cited

OTHER PUBLICATIONS

Walsh, S.L. et al. (May 1994). "Clinical Pharmacology of Buprenorphine: Ceiling Effects at High Doses," *Clinical Pharmacology & Therapeutics* 55(5):569-580.
Watanabe, K. (1996). "Rectal Absorption and Mucosal Irritation of Rectal Gels Containing Buprenorphine Hydrochloride Prepared with Water-Soluble Dietary Fibers, Xanthan Gum and Locust Bean Gum," *J. Controlled Release* 38:29-37.
Welsh, M.J. et al. (Mar. 1978). "Depression of Ventilation by Dopamine in Man: Evidence for an Effect on the Chemoreceptor Reflex," *J. Clin. Invest.* 61:708-713.
White, J. et al. (2009, e-pub. Apr. 28, 2009). "Open-label Dose-finding Trial of Buprenorphine Implants (Probuphine)® for Treatment of Heroin Dependence," *Drug and Alcohol Dependence* 103:37-43.
Whyte, C.R. et al. (1974). "Disulfiram Implant: A Controlled Trial," *Br. J. Psychiatry* 124:42-44.
Wilding, I.R. et al. (Apr. 30, 1996). "Pharmacokinetic Evaluation of Transdermal Buprenorphine in Man," *International Journal of Therapeutics* 132(1,2):81-87.
Wilson, A. et al (1980). "Disulfiram Implantation: A Trial Using Placebo Implants and Two Types of Controls," *J. Stud. Alcohol* 41(5):429-436.
Wilson, A. et al. (1978). "Disulfiram Implantation: A Placebo-Controlled Trial with Two-Year Follow-Up," *Journal of Studies on Alcohol* 39(5):809-819.
Wilson, A. et al. (1976). "Disulfiram Implantation: Placebo, Psychological Deterrent, and Pharmacological Deterrent Effects," *Br. J. Psychiatry* 129:277-280.
Winkelmüller, M. et al. (Sep. 1996). "Long-Term Effects of Continuous Intrathecal Opioid Treatment in Chronic Pain of Nonmalignant Etiology," *J. Neurosurg* 85:458-467.
Written Opinion mailed Sep. 18, 2008, for PCT Application No. PCT/US2007/012046, filed on May 18, 2007, 9 pages.
Yoburn, B.C. et al. (1986). "Pharmacokinetics and Pharmacodynamics of Subcutaneous Naltrexone Pellets in the Rat," *J. Pharmacol. Exp. Ther.* 237(1):126-130.
Zubieta, J-K. et al. (2000). "Buprenorphine-Induced Changes in Mu-opioid Receptor Availability in Male Heroin-Dependent Volunteers: A Preliminary Study," *Neuropsychopharmacology* 23(3):326-334.
Final Office Action mailed on Jul. 22, 2008, for U.S. Appl. No. 10/815,481, filed Mar. 31, 2004, 19 pages.
Response to Non-Final Office Action submitted to the USPTO on Apr. 28, 2008, for U.S. Appl. No. 10/815,481, filed Mar. 31, 2004, 22 pages.
Non-Final Office Action mailed on Nov. 29, 2007, for U.S. Appl. No. 10/815,481, filed Mar. 31, 2004, 8 pages.
Non-Final Office Action mailed on Jan. 20, 2006, for U.S. Appl. No. 10/453,377, filed Jun. 2, 2003, 9 pages.
Amendment in Response to Non-Final Office Action submitted to the USPTO on May 23, 2006, for U.S. Appl. No. 10/453,377, filed Jun. 2, 2003, 19 pages.
Final Office Action mailed on Jul. 25, 2006, for U.S. Appl. No. 10/453,377, filed Jun. 2, 2003, 9 pages.
Interview Summary mailed on Sep. 18, 2006, for U.S. Appl. No. 10/453,377, filed Jun. 2, 2003, 16 pages.
Amendment submitted to the USPTO on Sep. 19, 2006, for U.S. Appl. No. 10/453,377, filed Jun. 2, 2003, 15 pages.
Non-Final Office Action mailed on Dec. 11, 2006, for U.S. Appl. No. 10/453,377, filed Jun. 2, 2003, 6 pages.
Interview Summary mailed on Feb. 27, 2007, for U.S. Appl. No. 10/453,377, filed Jun. 2, 2003, 2 pages.
Amendment in Response to Non-Final Office Action submitted to the USPTO on May 8, 2007, for U.S. Appl. No. 10/453,377, filed Jun. 2, 2003, 12 pages.
Final Office Action mailed on Jul. 13, 2007, for U.S. Appl. No. 10/453,377, filed Jun. 2, 2003, 7 pages.
Amendment after Request for Continued Examination submitted to the USPTO on Oct. 31, 2007, for U.S. Appl. No. 10/453,377, filed Jun. 2, 2003, 8 pages.

Non-Final Office Action mailed on Jan. 15, 2008, for U.S. Appl. No. 10/453,377, filed Jun. 2, 2003, 6 pages.
Interview Summary mailed on Jun. 12, 2008, for U.S. Appl. No. 10/453,377, filed Jun. 2, 2003, 3 pages.
Amendment in Response to Non-Final Office Action submitted to the USPTO on Jul. 15, 2008, for U.S. Appl. No. 10/453,377, filed Jun. 2, 2003, 15 pages.
Final Office Action mailed on Oct. 29, 2008 for U.S. Appl. No. 10/453,377, filed Jun. 2, 2003, 8 pages.
Interview Summary mailed on Dec. 5, 2008 for U.S. Appl. No. 10/453,377, filed Jun. 2, 2003, 4 pages.
Amendment after Request for Continued Examination submitted to the USPTO on Jan. 30, 2009, for U.S. Appl. No. 10/453,377, filed Jun. 2, 2003, 9 pages.
Supplemental Response submitted to the USPTO on Mar. 16, 2009, for U.S. Appl. No. 10/453,377, filed Jun. 2, 2003, 5 pages.
Non-Final Office Action mailed on May 13, 2009 for U.S. Appl. No. 10/453,377, filed Jun. 2, 2003, 9 pages.
Amendment in Response to the Non-Final Office Action submitted on Sep. 4, 2009, for U.S. Appl. No. 10/453,377, filed Jun. 2, 2003, 13 pages.
Notice of Allowance mailed on Nov. 30, 2009 for U.S. Appl. No. 10/453,377, filed Jun. 2, 2003, 10 pages.
Non-Final Office Action mailed on Mar. 23, 2011 for U.S. Appl. No. 11/801,302, filed May 8, 2007, 9 pages.
Amendment in Response to the Non-Final Office Action submitted on Sep. 23, 2011, for U.S. Appl. No. 11/801,302, filed May 8, 2007, 8 pages.
Final Office Action mailed on Nov. 3, 2011 for U.S. Appl. No. 11/801,302, filed May 8, 2007, 7 pages.
Non-Final Office Action mailed on Apr. 15, 2011 for U.S. Appl. No. 12/341,766, filed Dec. 22, 2008, 21 pages.
Amendment in Response to the Non-Final Office Action submitted on Sep. 15, 2011 for U.S. Appl. No. 12/341,766, filed Dec. 22, 2008, 18 pages.
Final Office Action mailed on Nov. 25, 2011 for U.S. Appl. No. 12/341,766, filed Dec. 22, 2008, 25 pages.
Interview Summary mailed on Jul. 28, 2011 for U.S. Appl. No. 12/119,334, filed May 12, 2008, 3 pages.
Non-Final Office Action mailed on Dec. 15, 2011 for U.S. Appl. No. 12/119,334, filed May 12, 2008, 12 pages.
Non-Final Office Action mailed on Jan. 9, 2008 for U.S. Appl. No. 10/856,178, filed May 27, 2004, 5 pages.
Amendment in Response to Non-Final Office Action submitted on Jul. 8, 2008 for U.S. Appl. No. 10/856,178, filed May 27, 2004, 16 pages.
Final Office Action mailed on Jul. 7, 2009 for U.S. Appl. No. 10/856,178, filed May 27, 2004, 22 pages.
Interview Summary mailed on Apr. 17, 2009 for U.S. Appl. No. 10/815,481, filed Mar. 31, 2004, 2 pages.
Substance of Interview mailed on May 14, 2009, for U.S. Appl. No. 10/815,481, filed Mar. 31, 2004, 3 pages.
Suboxone and Subutex [drug label]. Reckitt Benckiser Pharmaceuticals, Inc., Richmond, VA, 2002, located at <http://www.fda.gov/Drugs/DrugSafety/PostmarketDrugSafetyInformationforPatientsandProviders/ucm191520.htm>, last visited on Apr. 23, 2014, nineteen pages.
Van Laarhoven, J.A.H. et al. (2002). "Effect of Supersaturation and Crystallization Phenomena on the Release Properties of a Controlled Release Device Based on EVA Copolymer," *Journal of Controlled Release* 82:309-317.
Non-Final Office Action mailed on May 23, 2013 for U.S. Appl. No. 13/691,379, filed Nov. 30, 2012, 11 pages.
Interview Summary mailed on Nov. 12, 2013 for U.S. Appl. No. 13/691,379, filed Nov. 30, 2012, 3 pages.
Response to Non-Final Office Action submitted to the USPTO on Nov. 21, 2013 for U.S. Appl. No. 13/691,379, filed Nov. 30, 2012, 9 pages.
Final Office Action mailed on Jan. 17, 2014 for U.S. Appl. No. 13/691,379, filed Nov. 30, 2012, 9 pages.

* cited by examiner

Figure 1

Figure 2

IMPLANTABLE POLYMERIC DEVICE FOR SUSTAINED RELEASE OF DOPAMINE AGONIST

CROSS-REFERENCE TO RELATED APPLICATIONS

This application is a continuation application of U.S. patent application Ser. No. 12/119,334, filed May 12, 2008, which is a divisional application of U.S. patent application Ser. No. 10/815,481, filed Mar. 31, 2004, which claims the benefit of U.S. provisional application No. 60/459,315, filed on Mar. 31, 2003, all of which are incorporated herein by reference in their entirety.

TECHNICAL FIELD

The invention provides a nonbioerodible, polymeric device for subcutaneous implantation and sustained release of dopamine agonist for treatment of Parkinson's disease and other conditions for which administration of a dopamine agonist is therapeutically beneficial.

BACKGROUND OF THE INVENTION

Parkinson's disease, a progressive neurodegenerative disorder, is characterized by loss of neurons that synthesize and release dopamine. This loss of dopaminergic neurons manifests itself in symptoms such as rigidity, resting tremors (shaking), poverty of movement (akinesia), slowness of movement (bradykinesis), and changes in gait and posture. Treatment of Parkinson's disease generally is based on therapeutic administration of substances that can compensate for the lack of dopaminergic neurotransmission due to the loss of dopamine-secreting neurons. A classic treatment regime includes chronic oral administration of levodopa, which is decarboxylated in the brain to form dopamine. Often, after several years of treatment with levodopa, abnormalities emerge, including involuntary movements during the "on" phase of clinical improvement and re-emergence of Parkinson's-type symptoms during "off" phases.

Apomorphine, an effective agonist at both dopamine receptors in the nervous system, has been used for treatment of Parkinson's disease in patients that have become resistant to or have developed adverse side effects with associated with chronic levodopa therapy. Typically, due to its short duration of effectiveness, apomorphine is administered by repeated subcutaneous injections or continuous parenteral infusion via a pump. These means of administration are inconvenient, in the case of subcutaneous injection, and technically difficult, in the case of pump administration, especially for Parkinson's patients whose dexterity is impaired due to the disease itself and the movements associated with chronic levodopa treatment. Apomorphine may also be administered transdermally (U.S. Pat. No. 5,562,917), intranasally (U.S. Pat. No. 5,756, 483), as a topically-applied gel (U.S. Pat. No. 5,939,094), or sublingually (U.S. Pat. No. 5,994,363). None of these methods permits continuous administration over long periods of time.

Dopamine agonists have also been used for treatment of parkinsonism which results from central nervous system injury by toxin exposure or a disease condition such as encephalitis, erectile dysfunction, restless leg syndrome, and hyperprolactinemia.

There is a need for an improved means of administration that would permit continuous dosing of dopamine agonists over an extended period of time of several months or longer, without the adverse side effects associated with peaks and troughs in plasma levels due to discontinuous dosing, or reliance on cumbersome mechanical equipment such as a pump.

BRIEF SUMMARY OF THE INVENTION

The invention provides compositions (i.e., implantable polymeric devices), methods, and kits for administration of one or more dopamine agonists to a mammal in need thereof.

In one aspect, the invention provides an implantable device for administration of a dopamine agonist to a mammal in need thereof. The implantable device includes at least one dopamine agonist encapsulated in a biocompatible, nonerodible polymeric matrix. After subcutaneous implantation in a mammal, an implantable device of the invention releases dopamine agonist continuously in vivo through pores that open to the surface of the matrix at a rate that results in a plasma level of at least about 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 5, or 10 ng/ml in various embodiments. In some embodiments, an implantable device of the invention includes ethylene vinyl acetate (EVA) as a biocompatible, nonerodible polymer for formation of the polymeric matrix. In various embodiments, the vinyl acetate content of EVA used for preparation of the polymeric matrix is often about 2 to about 40, more often about 10 to about 35, most often about 30 to about 35%. In some embodiments, the vinyl acetate content is about 33%. An implantable device of the invention includes about 10 to about 85% dopamine agonist. In some embodiments, the dopamine agonist is apomorphine, lisuride, pergolide, bromocriptine, pramipexole, ropinerole, or rotigotine. In one embodiment, the dopamine agonist is apomorphine. The dopamine agonist is generally at least a dopamine D2 receptor agonist, but may also be an agonist for the D1 and/or D3 dopamine receptors. Implantable devices often release dopamine agonist continuously in vivo for at least about 3, 6, 9, 12, 15, 18, 21, or 24 months. In some embodiments, implantable devices of the invention are produced using an extrusion process, sometimes producing devices with dimensions of about 2 to about 3 mm in diameter and about 2 to about 3 cm in length, although other shapes and sizes are contemplated and are within the skill of the art. Often, an implantable device of the invention releases dopamine agonist at a rate of at least about 0.1 to about 10 mg/day at steady state in vitro or in vivo. In various embodiments, the implantable devices release dopamine agonist at a rate of at least about 0.01, 0.05, 0.1, 0.5, 1, 2, 3, 4, 5, 6, 7, 8, 9, or 10 mg/day in vitro or in vivo. In some embodiments, a dopamine-containing implantable device may further include an anti-inflammatory agent, for example a steroid, a nonsteroidal anti-inflammatory drug ("NSAID"), or an antihistamine, and/or an antioxidant within the polymeric matrix.

In another aspect, the invention provides a method for administration of a dopamine agonist to a mammal in need thereof. Methods of the invention include subcutaneous administration of at least one implantable device as described above. In some embodiments, the methods include subcutaneous implantation of a multiplicity of the devices. In methods of the invention, the device or devices release dopamine agonist at a steady state level that is therapeutically effective for treatment of a condition for which administration of a dopamine agonist is therapeutically beneficial, for example, Parkinson's disease, toxin- or disease-induced parkinsonism, erectile dysfunction, restless leg syndrome, or hyperprolactinemia. In some embodiments, the dopamine agonist is apomorphine, lisuride, pregolide, bromocriptine, pramipexole, ropinerole, or rotigotine. In one embodiment, the dopamine agonist is apomorphine. Typically, each device, or the combination of a multiplicity of devices, continuously releases at least about 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 5, 10, 25, 50, or 100 ng of dopamine agonist per ml of plasma at steady state. Generally, each device releases at least about 0.1 mg of dopamine agonist per day in vitro. In various embodiments, one or a multiplicity of devices is subcutaneously implanted in an individual, for example, on the upper arm, the back, and/or the abdomen.

In some embodiments, one or more anti-inflammatory agents are coadministered along with dopamine agonist. The anti-inflammatory agent may be encapsulated within the same polymeric device as dopamine agonist or in a separate polymeric device that does not contain dopamine agonist, or may be administered via a different route, such as orally or via injection, either simultaneously with implantation of the dopamine agonist-containing devices or at a different time, or on a different schedule such as for example multiple dosing of an oral or injectable formulation. In various embodiments, the anti-inflammatory agent may be a steroid, a NSAID, and/or an antihistamine. In some embodiments, an antioxidant is incorporated into the dopamine agonist-containing polymeric device and is coadministered along with dopamine agonist. In some embodiments, the methods of the invention include administration of another substance in conjunction with administration of dopamine agonist via an implanted polymeric device of the invention. Such substances include, but are not limited to, levodopa, dopamine agonists, catechol-O-methyltranserase inhibitors, or monoamine oxidase inhibitors, administered orally or intravenously.

In another aspect, the invention provides a kit for use in a method of administration of a dopamine agonist to a mammal in need thereof. Kits of the invention include at least one implantable device that includes dopamine agonist encapsulated in a biocompatible, nonerodible polymeric matrix, as described above, and instructions for use. In some embodiments, kits of the invention include a multiplicity of individual dopamine agonist-containing implantable devices.

BRIEF DESCRIPTION OF THE DRAWINGS

FIG. 1 shows the average cumulative release of apomorphine HCl ("ApoH") from implants loaded with 50%, 60%, or 70% ApoH and washed for 30 minutes (FIG. 1A), 60 minutes (FIG. 1B), or 120 minutes (FIG. 1C) in ethanol.

DETAILED DESCRIPTION OF THE INVENTION

The invention provides a biocompatible, nonerodible polymeric device, which permits controlled, sustained release of one or more dopamine agonists over extended periods of time when implanted subcutaneously in an individual in need of treatment.

Continuous release of a compound in vivo over an extended duration may be achieved via implantation of a device containing the compound encapsulated, i.e., dispersed, in a nonerodible polymeric matrix. Examples of implantable, nonerodible polymeric devices for continuous drug release are described in, e.g., U.S. Pat. Nos. 4,883,666, 5,114,719, and 5,601,835. Implantation of the device and extended release of dopamine agonist improves compliance with dosing regimens, eliminating the need for repeated injections, ingestion of pills or tablets, or manipulations associated with a mechanical diffusion pump. An implantable, sustained-release device according to the present invention also permits achievement of more constant blood levels of dopamine agonist than injectable or oral dosage forms, thereby permitting lower dosing levels than conventional means of administration, minimizing side effects, and improving therapeutic effectiveness.

Devices of the invention include one or more non-bioerodible polymers. Such polymers release compounds at linear rates for extended time periods of several months or longer, in contrast to bioerodible polymers, which do not exhibit linear release kinetics due to formation of channels in the matrix as it erodes, resulting in increased release rates over time. The present invention includes a biocompatible, nonerodible polymer that exhibits generally linear release kinetics for dopamine agonist in vivo, after an initial burst.

Implantable Polymeric Devices

The invention includes implantable devices for treatment of Parkinson's disease or other conditions for which administration of a dopamine agonists is therapeutically beneficial. Devices of the invention include one or more dopamine agonists encapsulated in a polymeric, nonerodible matrix.

"Dopamine agonist" as used herein refers to a compound which is capable of binding to one or more dopamine receptor subgroups, resulting in beneficial therapeutic effect in an individual treated with the agonist. The dopamine agonists described herein typically are agonists for at least the D2 subgroup of dopamine receptors, and may also be agonists for D1 and/or D3 receptors. In various embodiments, an implantable device of the invention includes apomorphine, lisuride, pergolide, bromocriptine, pramipexole, ropinerole, or rotigotine, or a combination or two or more of these dopamine agonists. In one embodiment, the implantable device includes apomorphine. "Apomorphine" refers to apomorphine and pharmaceutically acceptable salts thereof, such as for example, apomorphine HCl ("ApoH").

Incorporation of dopamine agonist into the polymeric matrix causes the formation of a series of interconnecting channels and pores that are accessible to the surface for release of the drug. When implanted subcutaneously, devices of the invention continuously release dopamine agonist for an extended period of time with a pseudo or near zero order release rate. After an initial burst following implantation, release rates are typically within about 10-20% of the steady state average.

As used herein, "nonerodible matrix" refers to a polymeric carrier that is sufficiently resistant to chemical and/or physical destruction by the environment of use such that the matrix remains essentially intact throughout the release period. The polymer is generally hydrophobic so that it retains its integrity for a suitable period of time when placed in an aqueous environment, such as the body of a mammal, and stable enough to be stored for an extended period before use. The ideal polymer must also be strong, yet flexible enough so that it does not crumble or fragment during use. Nonerodible matrices remain intact in vivo for extended periods of time, typically months or years. Drug molecules encapsulated in the matrix are released over time via diffusion through channels and pores in a sustained and predictable manner. The release rate can be altered by modifying the percent drug loading, porosity of the matrix, structure of the implantable device, or hydrophobicity of the matrix, or by adding a hydrophobic coating to the exterior of the implantable device.

Where appropriate, a coating that is impermeable to the drug is placed over at least a portion of the device to further regulate the rate of release. For example, a coating of a nonerodible polymeric material, e.g., EVA, or a coating of a nonerodible polymeric material with a lower drug loading than the remainder of the implantable device, may be used. Such a coating may be formed, for example, by co-extrusion with the device.

Typically, ethylene vinyl acetate copolymer (EVA) is used as the polymeric matrix, but other nonerodible materials may be used. Examples of other suitable materials include silicone, hydrogels such as crosslinked poly(vinyl alcohol) and poly(hydroxy ethylmethacrylate), acyl substituted cellulose acetates and alkyl derivatives thereof, partially and completely hydrolyzed alkylene-vinyl acetate copolymers, unplasticized polyvinyl chloride, crosslinked homo- and copolymers of polyvinyl acetate, crosslinked polyesters of acrylic acid and/or methacrylic acid, polyvinyl alkyl ethers, polyvinyl fluoride, polycarbonate, polyurethane, polyamide, polysulphones, styrene acrylonitrile copolymers, crosslinked poly(ethylene oxide), poly(alkylenes), poly(vinyl imidazole), poly(esters), poly(ethylene terephthalate), polyphosphazenes, and chlorosulphonated polyolefines, and combinations thereof.

Implantable devices of the invention are typically formulated with dopamine agonist loading of about 10% to about 85%. Devices are often formulated as compositions that include a polymeric matrix that includes EVA (33% acetate) and any of at least about 10, 20, 30, 40, 50, 55, 60, 65, 70, 75, or 80 to about 85%, or any of about 10 to about 20, about 20 to about 30, about 30 to about 40, about 40 to about 50, about 50 to about 60, about 60 to about 70, about 70 to about 80, or about 80 to about 85% dopamine agonist by weight. Devices may be produced using an extrusion process, wherein ground EVA is blended with dopamine agonist, melted, and extruded into rod-shaped structures. Rods are cut into individual implantable devices of the desired length, packaged, and sterilized prior to use. Other methods for encapsulating therapeutic compounds in implantable polymeric, nonerodible matrices are well known to those of skill in the art. Such methods include, for example, solvent casting (see, e.g., U.S. Pat. Nos. 4,883,666, 5,114,719, and 5,601,835). A skilled artisan would be able to readily determine an appropriate method of preparing such an implantable device, depending on the shape, size, drug loading, and release kinetics desired for a particular type of patient or clinical indication.

Devices of the invention are suitable for sustained release of dopamine agonist for treatment of idiopathic Parkinson's disease or another condition for which administration of dopamine agonist is therapeutically beneficial, such as, for example, toxin- or disease-induced parkinsonism, erectile dysfunction, restless leg syndrome, or hyperprolactinemia. As used herein, "sustained release" refers to the release of dopamine agonist such that the blood concentration remains within the therapeutic range but below toxic levels for an extended duration. Devices of the invention generally exhibit near zero-order pharmacokinetics in vivo, similar to kinetics achieved with an IV drip, but without the need for external medical equipment and personnel associated with intravenous methods. Generally, after implantation, the devices release therapeutically effective amounts of dopamine for periods of several months up to one year or longer.

Multiple implantable devices may be used, or the size and shape of the devices may be modified, to achieve a desired overall dosage. Implantable devices are often about 0.5 to about 10, more often about 1.5 to about 5, often about 2 to about 6, most often about 2 to about 3 cm in length, and are often about 0.5 to about 7, more often about 1.5 to about 5, most often about 2 to about 3 mm in diameter. An implantable device of the invention may release dopamine agonist in vitro or in vivo at a rate of about 0.01 to about 10, about 0.1 to about 10, about 0.25 to about 5, or about 1 to about 3 mg/day in vitro or in vivo. The release rate of implantable devices may also be modified by changing the vinyl acetate content in the EVA polymer matrix. The vinyl acetate content is often about 2 to about 40, more often about 10 to about 35, most often about 30 to about 35% by weight. In one embodiment, the vinyl acetate content is about 33% by weight.

In certain embodiments, devices of the invention may include other substances in addition to dopamine agonist to increase effectiveness of treatment and/or reduce inflammation at the site of administration, or to prevent oxidation of dopamine agonist(s). For example, an anti-inflammatory agent, such as for example, a steroid, examples of which include but are not limited to dexamethasone, triamcinolone, betamethasone, clobetasol, cortisone, hydrocortisone, or a pharmaceutically acceptable salt thereof, or a nonsteroidal anti-inflammatory agent ("NSAID"), examples of which include but are not limited to diclofenac potassium diclofenac sodium, diclofenac sodium with misoprostol, diflunisal, etodolac, fenoprofen calcium, flurbiprofen, ibuprofen, indomethacin, ketoprofen, meclofenamate sodium, mefenamic acid, meloxicam, nabumetone, naproxen, naproxen sodium, oxaprozin, piroxicam, sulindac, tolmetin, COX-2 inhibitors (e.g., celecoxib, rofecoxib, valdecoxib), acetylated salicylates (e.g., aspirin), nonacetylated salicylates (e.g., choline, magnesium, and sodium salicylates, salicylate), and/or an antihistamine, examples of which include but are not limited to loratadine ("LT"), astemizole, cetrizine dihydrochloride, chlorpheniramine, dexochlorpheniramine, diphenhydramine, mebhydrolin napadisylate, pheniramine maleate, promethazine, or terfenadine, may be encapsulated within an implant to prevent or reduce local inflammation at the site of administration. Any of these agents, or a combination, may be included in the same implant(s) as dopamine agonist or alternatively, may be incorporated into one or more separate implants that do not include dopamine agonist. An antioxidant, e.g., ascorbic acid, sodium metabisulfite, glutathione, may be included in the same implant as dopamine agonist to prevent or reduce oxidation of dopamine agonist during preparation, storage, and/or administration of the implant.

Methods of the Invention

The invention provides methods for treatment of idiopathic Parkinson's disease or toxin- or disease-induced parkinsonism, or any other condition for which administration of a dopamine agonist is therapeutically beneficial, e.g., erectile dysfunction, restless leg syndrome, or hyperprolactinemia. "Parkinsonism" as used herein includes conditions resulting from injury to the central nervous system that cause an individual to exhibit symptoms similar to those of Parkinson's disease. Parkinsonism may result, for example, from toxin exposure, for example, carbon monoxide or manganese poisoning or MPTP administration, or from a disease condition such as encephalitis.

Methods of the invention include subcutaneous administration of one or more polymeric implantable devices which each include one or more dopamine agonists encapsulated within a biocompatible, nonerodible polymeric matrix, e.g., EVA, and release of the dopamine agonist(s) in a controlled manner over an extended period of time through multiple pores that open to the surface of the implantable device(s). Often, implantable devices are produced via an extrusion process, as described above.

In various embodiments, the method includes administration of apomorphine, lisuride, pergolide, bromocriptine, pramipexole, ropinerole, or rotigotine, or a combination or two or more of these dopamine agonists. A combination of dopamine agonists may be administered from the same implantable device(s) or may be administered from separate implantable devices. In one embodiment, the method includes administration of apomorphine.

Implantable devices are administered by subcutaneous implantation to an individual in need of treatment with a dopamine agonist. As used herein, "individual" refers to a mammal, such as a human, in need of treatment for Parkinson's disease or parkinsonism, or another condition for which dopamine administration is therapeutically beneficial. Generally, implantable devices are administered by subcutaneous implantation at sites including, but not limited to, the upper arm, back, or abdomen of an individual. Other suitable sites for administration may be readily determined by a medical professional. Multiple implantable devices may be administered to achieve a desired dosage for treatment.

Typically, in a treatment method of the invention, an implantable device or a multiplicity of devices is administered that will release dopamine at a rate that will maintain a therapeutically effective plasma level for an extended period of time of at least about 3, 6, 9, 12, 15, 18, 21, or 24 months. Often, the duration of implantation, with continuous release of dopamine agonist, is from about 3 months to about 2 years, about 3 months to about 1 year, about 3 months to about 9 months, or about 3 months to about 6 months.

The desired dosage rate will depend upon factors such as the underlying condition for which dopamine agonist is being administered, and the physiology of a particular patient, but will be readily ascertainable to physicians. Dopamine agonist is desirably released from one or a multiplicity of implanted devices at a rate that maintains plasma levels of the drug(s) at a therapeutically effective level. Maintenance of dopamine agonist at a fairly constant plasma level often permits dosing at a lower level than with other therapies, such as oral administration.

As used herein, "therapeutically effective amount" or "therapeutically effective level" refers to the amount of dopamine agonist that will render a desired therapeutic outcome, e.g., a level or amount effective to reduce symptoms of Parkinson's disease and/or increase periods of therapeutic effectiveness ("on" periods) for a patient undergoing chronic dopaminergic therapy for idiopathic Parkinson's disease or toxin- or disease-induced parkinsonism, or beneficial treatment, i.e., reduction or alleviation of adverse or undesirable symptoms of a condition treatable with a dopamine agonist, such as erectile dysfunction, restless leg syndrome, or hyperprolactinemia. For treatment of Parkinson's disease or parkinsonism, effectiveness is often associated with reduction in "on"/"off" fluctuations associated with a particular Parkinson's disease treatment regime, such as for example, chronic levodopa administration. An amount that is "therapeutically effective" for a particular patient may depend upon such factors as a patient's age, weight, physiology, and/or the particular symptoms or condition to be treated, and will be ascertainable by a medical professional.

When multiple devices are administered, the combination of the devices releases dopamine agonist at a rate that will achieve a therapeutically effective plasma level. Often, a desirable steady-state plasma level of dopamine agonist in methods of the invention is in the range of about 0.005 to about 100 ng/ml, about 0.01 to about 100 ng/ml, about 0.05 to about 0.65 ng/ml, about 0.2 to about 0.65 ng/ml, about 0.2 to about 45 ng/ml, or about 1 to about 20 ng/ml. In various embodiments, an implantable device of the invention may release dopamine agonist in vivo at a rate that results in a plasma level of at least about 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 5, or 10 ng/ml at steady state. A total release rate from one or a multiplicity of implanted devices that results in delivery of a therapeutically effective amount of dopamine agonist on a daily basis is typically about 0.01 to about 10 mg/day, often about 0.25 to about 5 mg/day, sometimes about 1 to about 3 mg/day, but may be modified depending upon the symptomology involved and the particular patient being treated. For example, for treatment of Parkinson's disease with apomorphine or another dopamine agonist described herein, one or more implantable devices may be used with a total release rate of about 0.01 to about 10 mg/day, about 0.25 to about 5 mg/day, or about 1 to about 3 mg/day apomorphine.

It is anticipated that the implantable devices of the invention will alleviate compliance difficulties, as described above. In methods of the invention, long term continuous release of dopamine agonist generally reduces or eliminates the peaks and troughs of blood concentration associated with other formulations such as oral or injectable dosage forms, which permits dosing at a lower level than traditional treatment regimens. This often reduces or alleviates adverse side effects associated with higher dosages, for example, nausea, vomiting, orthostatic hypotension, hallucinations, delirium, or dyskinesia.

In some methods of the invention, dopamine is administered via an implantable device of the invention in conjunction with another therapy. For example, for Parkinson's or parkinsonism, dopamine agonist may be administered via implantable devices of the invention in conjunction with levodopa, dopamine agonists, catechol-O-methyltransferase (COMT) inhibitors, or monoamine oxidase (MAO) inhibitors, administered orally or intravenously.

Some methods of the invention include coadministration of another substance or substances in conjunction with dopamine agonist. For example, an anti-inflammatory agent or agents, such as a steroid, a NSAID, and/or an antihistamine, may be administered via an implantable device, by local, systemic, or subcutaneous injection, or orally, in conjunction with administration of dopamine agonist in an implantable device of the invention, to reduce or prevent inflammation caused by the agonist(s) at the site of administration of the implant. When the anti-inflammatory agent(s) is administered via an implantable device, it may be included in the same implant as dopamine agonist or in a separate implantable device. An implantable device may include one or more of the anti-inflammatory agents described above. The amount of anti-inflammatory agent administered is an amount expected to be effective to reduce local inflammation associated with administration of dopamine agonist in an implanted device of the invention.

In some methods of the invention, an antioxidant may be included in the dopamine agonist implant to prevent oxidation of the dopamine agonist(s) during preparation, storage, and/or administration of the implant. Generally, the amount of antioxidant incorporated into the implant is an amount sufficient to prevent oxidation of at least a portion, typically substantially all of the dopamine agonist in the implant.

Methods of the invention may be used to treat any subpopulation of Parkinson's disease patients, including, for example, "de novo" patients, e.g., patients who have not previously received treatment, "early stage" patients, e.g., patients who have been treated for a short period of time with another therapy such as levodopa administration but who are not exhibiting adverse side effects from the other therapy, "late stage" patients, e.g., patients who are exhibiting side effects associated with chronic treatment with another therapeutic substance such as levodopa, and "fluctuators," e.g., patients for whom treatment with another substance such as levodopa fluctuates in effectiveness in an "on"/"off" manner.

Methods of the invention may be used, for example, to decrease motor fluctuations and dyskinesias for treatment of "late stage" patients with motor fluctuations. Continuous dosing via an implantable device of the invention may decrease "off" time and decrease dyskinesias. The methods may also be used, for example, to prevent motor fluctuations and dyskinesias in "early stage" patients who are undergoing pharmacologic therapy for the first time. This group often received monotherapy with a dopamine agonist. Administration via an implantable device of the invention may allow continuous dopamine agonist receptor stimulation, thus decreasing the risk of motor fluctuations and dyskinesias later in treatment. The methods may also be used, for example, to prevent motor fluctuations and dyskinesias in patients on dopamine agonist monotherapy who require l-dopa supplementation. Since it is difficult to administer l-dopa with linear dosing kinetics, and motor complications often emerge when l-dopa is administered, continuous dosing via the implantable devices of the invention may allow continuous dopamine agonist receptor stimulation and decrease the risk of motor fluctuations and dyskinesias at this point in treatment.

Kits

The invention also provides kits for use in treatment of Parkinson's disease or another condition for which dopamine agonist administration is therapeutically beneficial, as described above. The kits contain at least one implantable, nonerodible device of the type herein described, capable of delivering long-term therapeutic levels of dopamine agonist, in suitable packaging, along with instructions providing information to the user and/or health care provider regarding subcutaneous implantation and use of the system for treating a condition for which dopamine agonist administration is therapeutically beneficial, such as, for example, Parkinson's disease, toxin- or disease-induced parkinsonism, erectile dysfunction, restless leg syndrome, or hyperprolactinemia. Kits may also include literature discussing performance of the implantable devices of the invention.

In various embodiment, kits of the invention may include implantable devices that include apomorphine, lisuride, pergolide, bromocriptine, pramipexole, ropinerole, or rotigotine, or combinations of any of these dopamine agonists in the same or separate polymeric implants. In one embodiment, a kit includes one or more implantable devices that include encapsulated apomorphine.

Kits may include a delivery system, i.e., one or a multiplicity of implantable devices, capable of providing sustained release of therapeutic levels of dopamine agonist, e.g., about 0.005 to about 100 ng/ml, about 0.01 to about 100 ng/ml, about 0.05 to about 0.65 ng/ml, about 0.2 to about 0.65 ng/ml, about 0.2 to about 45 ng/ml, or about 1 to about 20 ng/ml, for at least about 3 months. Kits of the invention may include implantable devices each capable of in vivo release of dopamine agonist such that a plasma level of at least about 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 5, 10, 25, 45, or 100 ng/ml is achieved at steady state. Kits of the invention may include a delivery system capable of releasing about 0.1 to about 10, about 0.25 to about 5, or about 1 to about 3 mg/day dopamine agonist in vitro or in vivo.

The device(s) in a kit may include one or more substances in addition to dopamine agonist, such as one or more an anti-inflammatory agents, such as a steroid, NSAID, or antihistamine, and/or an antioxidant.

In kits of the invention, an implantable device or devices may be preloaded into an apparatus or apparatuses suitable for subcutaneous implantation of the device(s) into a patient, such as, for example, syringes or trocars.

EXAMPLES

The following examples are intended to illustrate but not limit the invention.

Example 1

Materials and Methods

Materials

The following materials were used:
Apomorphine HCl, supplied by Hawkins, Inc.
Triamcinolone Acetonide, supplied by Spectrum
Glutathione, supplied by Aldrich, St. Louis, Mo.
Ethylene vinyl acetate copolymer, 33% vinyl acetate, supplied by Southwest Research Institute, San Antonio, Tex.
Methanol, ChromAR HPLC Grade, supplied by Mallinckrodt, St. Louis, Mo.
Acetonitrile, ChromAR HPLC Grade, supplied by Mallinckrodt, St. Louis, Mo.
Trifluoro Acetic Acid, 99%, Spectrochemical grade, supplied by Aldrich Chemicals, St. Louis, Mo.
Sodium Dodecyl Sulfate, 99%, supplied by EM Science
Ethanol, supplied by Mallinckrodt, St. Louis, Mo.

HPLC Assays

An HPLC method was used to determine the rate of in vitro release of apomorphine HCl ("ApoH") or loratidine ("LA") from the implants. Chromatography was performed using a Zorbax SB-C18 (250 mm×4.6 mm) column and 60% 0.1 trifluoro acetic acid in water, 15% methanol, 25% acetonitrile as the mobile phase, and a flow rate of 1 ml/min. The injection volume was 10 µl Detection was accomplished by means of a UV/VIS detector at a wavelength of 270 nm. Instrument control and data acquisition were facilitated using a Waters Millennium (V 2.15) software package. The external calibration was obtained using ApoH or LA standard solutions.

Preparation of Implantable Devices

Implantable devices were prepared using an extrusion process in a Microtruder device (Rancastle, RC-025-CF-RF). In order to facilitate feeding into the extruder and to enable mixing of apomorphine and other substances to be incorporated into the implants, EVA was ground into smaller particle sizes prior to extrusion. The extrusion process was performed under argon gas to prevent oxidation of apomorphine. All blends of copolymer and drug(s) were prepared by rolling in a 120 ml amber bottle for approximately 10 minutes. The blend was then fed through the Microtruder. Parameters that were used for extrusion of ApoH/EVA implants are shown in Table 1, and parameters used for extrusion of implants that included triancinolone ("TA"), glutathione ("GSH"), and/or LA are shown in Table 2.

TABLE 1

Parameters for Extrusions of APO/EVA Implants

| Formulations | Zone Temperature (° F.) | | | |
|---|---|---|---|---|
| (Weight Percentage) | 1 | 2 | 3 | Die |
| APO/EVA (50:50) | 180 | 185 | 190 | 185 |

TABLE 1-continued

Parameters for Extrusions of APO/EVA Implants

| Formulations (Weight Percentage) | Zone Temperature (° F.) | | | |
|---|---|---|---|---|
| | 1 | 2 | 3 | Die |
| APO/EVA (60:40) | 185 | 195 | 200 | 195 |
| APO/EVA (70:30) | 215 | 230 | 240 | 250 |

TABLE 2

Parameters for Extrusions of APO/EVA/TA/GSH Implants

| Formulations (Weight Percentage) | Zone Temperature (° F.) | | | |
|---|---|---|---|---|
| | 1 | 2 | 3 | Die |
| APO/EVA (60:40) | 190 | 195 | 205 | 200 |
| APO/TA/EVA (60:10:30) | 215 | 230 | 240 | 248 |
| APO/TA/GSH/EVA (60:8:2:30) | 215 | 235 | 245 | 255 |
| APO/LA/EVA (49:21:30) | 215 | 226 | 232 | 230 |

All of the materials used during the extrusion process were protected from light to prevent light-catalyzed oxidation. The extruder was set to the required temperatures and allowed to reach equilibrium. After the extruder reached equilibrium, approximately 15 grams of blend were extruded and cut into 18-inch rods. The diameter was measured at 2.4 mm. The rods were then cut to the desired implant length of 26 mm.

The implants were then washed by placing them on an aluminum screen and immersing them in ethanol (approximately 50 ml per implant). The implants were washed for approximately 30, 60, or 120 minutes in the ethanol bath. The washed implants were air dried for 10 minutes and oven dried at 40° C. for 1 hour before drying in a vacuum over for 24 hours at 30° C. The implants were packaged into 20 ml glass vials in the presence of argon gas, sealed, and then sterilized by gamma irradiation.

Example 2

In Vitro Characterization of Extruded Implantable Devices

Extruded rods prepared as described above were characterized for total drug load and for rate of drug release.

Assessment of Drug Loading

Implants prepared with 70% ApoH:30% EVA were cut into 2 mm pieces, accurately weighed, and placed into 250 ml volumetric flasks. Approximately 200 ml of methanol was added to each flask and the solution was continuously stirred at room temperature until the implants was dissolved. The solution was then assayed for drug content.

The average ApoH content for unwashed, washed, and sterilized rods was between 66.9 and 67.9% ApoH, corresponding to 95.6 to 97% recovery.

Assessment of Drug Release

Experiments were performed to determine the rate of apomorphine released from the extruded rods. The medium for these studies was 0.5% sodium dodecyl sulfate ("SDS"). Preweighed rods were placed in 100 ml screw cap jars containing 50 ml of medium and placed on an orbital shaker. The orbital shaker was housed in an incubator maintained at 37° C. Sampling was performed by replacing the medium periodically. The samples obtained were analyzed by HPLC.

Figure 1:
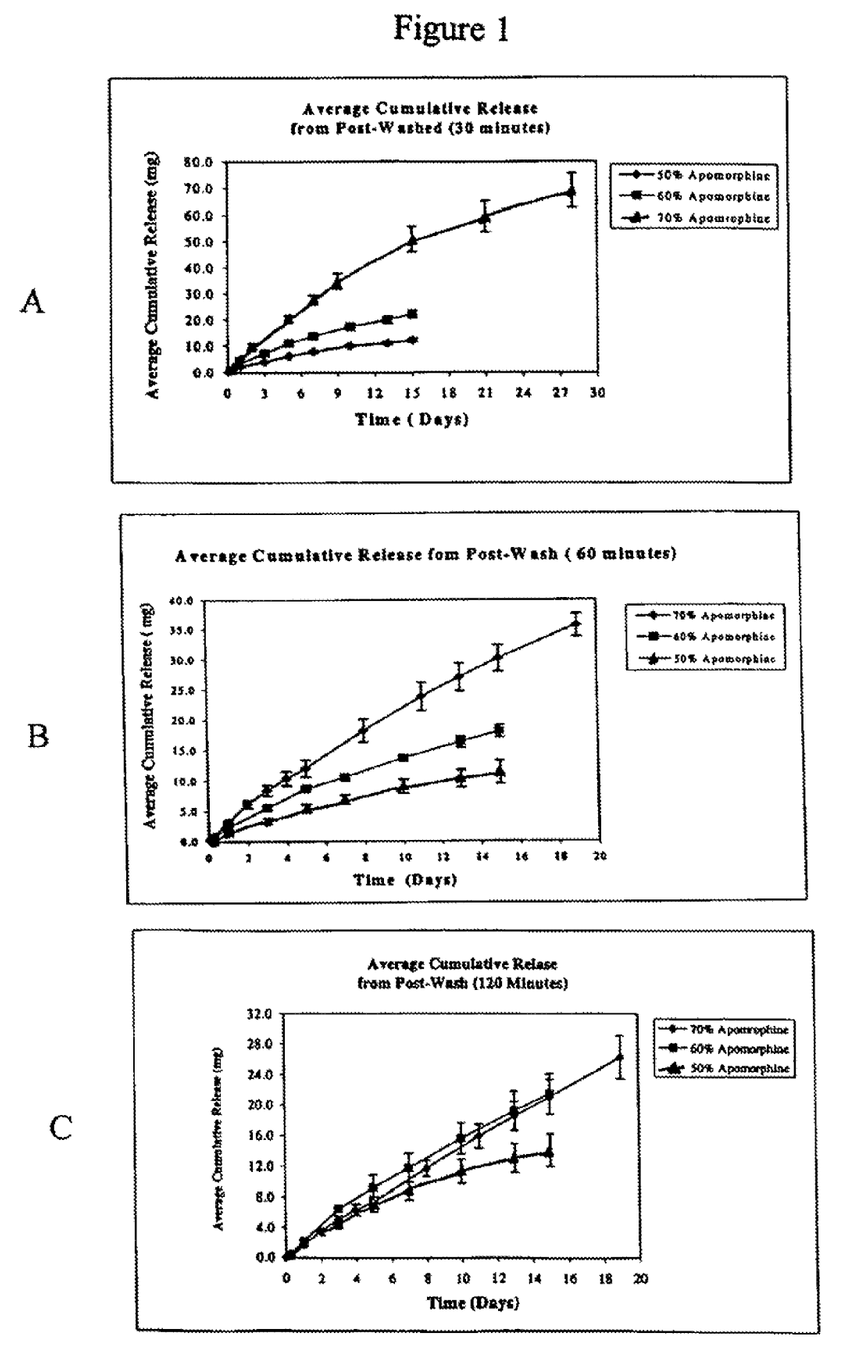
FIG. 1 depicts in vitro release of apomorphine over time.

FIG. 1 shows the release of apomorphine from implants that have been loaded with 50, 60, or 70% apomorphine and that have been washed for 30, 60, or 120 minutes. The in vitro release data indicate that the implants released a high amount of apomorphine during the first few days, then reached steady state between about 3 and 7 days. As the drug load increased, the rate of release ApoH increased for implants washed up to one hour. The data from implants washed for 2 hours showed no significant difference in release rate for the different drug loading levels.

Figure 2:
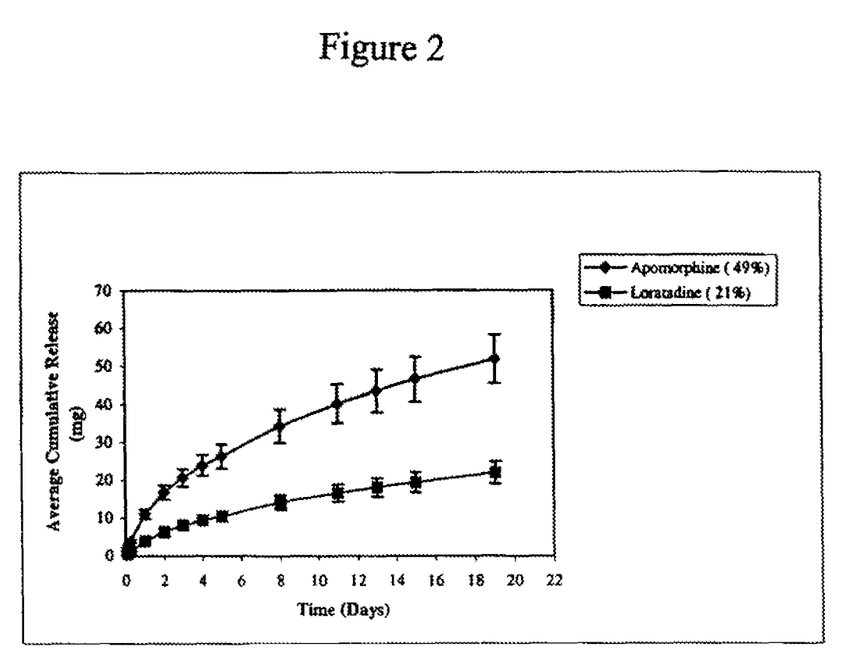
FIG. 2 depicts in vitro release of ApoH and loratidine ("LA") over time from an implant loaded with 49% ApoH and 21% LA.

FIG. 2 shows the release of ApoH and LA from a 49% ApoH/21% LA/EVA implant. Both ApoH and LA reached steady state release rates within about 3 days.

Example 3

In Vivo Evaluation of Drug Loaded Implantable Devices

Four MPTP-lesioned, L-DOPA-naïve cynomolgus monkeys were administered three 2.4 mm diameter×2.6 cm length rod-shaped implantable devices prepared as described above, each containing 33% vinyl acetate and loaded with 98 mg±10% apomorphine HCl (68.5% apomorphine). Devices were implanted between the shoulder blades using a trocar. For comparison, three additional MPTP-lesioned, L-DOPA-naïve monkeys received pulsatile daily subcutaneous injections of apomorphine at a dosage of 0.2 mg/kg, which is the minimally-effective dose to achieve "ON" status in the animal.

All of the monkeys that received apomorphine implants were continuously in an "ON" state within one day after implantation, with an average steady state apomorphine level of approximately 0.5-1.0 ng/ml achieved after an initial burst. In contrast, animals that received pulsatile injections were "ON" for only approximately 90 minutes after each administration of apomorphine.

After 8.3 days (range 7-10) of daily apomorphine injections, all animals in the pulsatile injection group developed dyskinesias. However, in the implant group, no animal developed dyskinesia for the duration of the treatment (up to six months). The apomorphine EVA implants provided continuous plasma levels of apomorphine, allowing for continuous stimulation of striatal dopaminergic receptors without onset of dyskinesia, for the six month duration of the evaluation.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention, which is delineated by the appended claims.

All publications, patents, and patent applications cited herein are hereby incorporated by reference in their entirety.

We claim:

1. An implantable device for subcutaneous administration of a dopamine agonist to a mammal in need thereof, comprising a dopamine agonist and a biocompatible, nonerodible polymeric matrix,
    wherein said dopamine agonist is encapsulated within said matrix,
    wherein the polymeric matrix comprises ethylene vinyl acetate copolymer (EVA), wherein the implantable device is produced by an extrusion process, wherein said dopamine agonist and the polymer are blended, melted, and extruded into a structure, wherein the implantable device further comprises a coating of EVA having a lower dopamine agonist loading than the remainder of the implantable device;

wherein the implantable device is washed, wherein the dopamine agonist is selected from the group consisting of lisuride, pergolide, bromocriptine, pramipexole, ropinirole, and rotigotine, and wherein when said implantable device is implanted subcutaneously in said mammal, said dopamine agonist is continuously released in vivo over a sustained period of time through pores that open to the surface of said matrix at a rate that results in a steady state plasma level of at least about 0.01 ng/ml for the sustained period of time, wherein the sustained period of time is at least about 3 months.

2. An implantable device according to claim 1, wherein said EVA comprises about 33% vinyl acetate.

3. An implantable device according to claim 1, comprising about 10 to about 85% dopamine agonist.

4. An implantable device according to claim 1, wherein said dopamine agonist is selected from the group consisting of lisuride, pergolide, and bromocriptine.

5. An implantable device according to claim 1, wherein said dopamine agonist is ropinirole.

6. An implantable device according to claim 1, wherein said dopamine agonist is pramipexole.

7. An implantable device according to claim 1, wherein said dopamine agonist is rotigotine.

8. An implantable device according to claim 1, comprising dimensions of about 2 to about 3 mm in diameter and about 2 to about 3 cm in length.

9. An implantable device according to claim 8, wherein said implantable device releases about 0.1 to about 10 mg of dopamine agonist per day in vitro.

10. An implantable device according to claim 1, further comprising an anti-inflammatory agent encapsulated within said matrix.

11. An implantable device according to claim 10, wherein said anti-inflammatory agent is a steroid.

12. An implantable device according to claim 10, wherein said anti-inflammatory agent is a nonsteroidal anti-inflammatory drug ("NSAID").

13. An implantable device according to claim 10, wherein said anti-inflammatory agent is an antihistamine.

14. An implantable device according to claim 1, further comprising an antioxidant encapsulated within said matrix.

15. An implantable device for subcutaneous administration of a dopamine agonist to a mammal in need thereof, comprising a dopamine agonist and a biocompatible, nonerodible polymeric matrix, wherein said dopamine agonist is encapsulated within said matrix, wherein the polymeric matrix comprises ethylene vinyl acetate copolymer (EVA), wherein the implantable device is produced by an extrusion process, wherein said dopamine agonist and the polymer are blended, melted, and extruded into a structure, wherein the implantable device further comprises a coating of EVA having a lower dopamine agonist loading than the remainder of the implantable device;

wherein the implantable device is washed, wherein the dopamine agonist is selected from the group consisting of lisuride, pergolide, bromocriptine, pramipexole, ropinirole, and rotigotine, and wherein when said implantable device is subcutaneously implanted in a mammal, said dopamine agonist is continuously released in vivo over a sustained period of time through pores that open to the surface of said matrix at a rate of at least about 0.1 mg of dopamine agonist per day at steady state, wherein the sustained period of time is at least about 3 months.

16. An implantable device according to claim 15, wherein said EVA comprises 33% vinyl acetate.

17. An implantable device according to claim 15, comprising about 10 to about 85% dopamine agonist.

18. An implantable device according to claim 15, wherein said dopamine agonist is selected from the group consisting of lisuride, pergolide, and bromocriptine.

19. An implantable device according to claim 15, wherein said dopamine agonist is ropinirole.

20. An implantable device according to claim 15, wherein said dopamine agonist is pramipexole.

21. An implantable device according to claim 15, wherein said dopamine agonist is rotigotine.

22. An implantable device according to claim 15, further comprising an anti-inflammatory agent encapsulated within said matrix.

23. An implantable device according to claim 22, wherein said anti-inflammatory agent is a steroid.

24. An implantable device according to claim 22, wherein said anti-inflammatory agent is a nonsteroidal anti-inflammatory drug (NSAID).

25. An implantable device according to claim 22, wherein said anti-inflammatory agent is an antihistamine.

26. An implantable device according to claim 15, further comprising an antioxidant encapsulated within said matrix.

27. A method for subcutaneous administration of a dopamine agonist to a mammal in need thereof, the method comprising administering at least one implantable device according to claim 1.

28. A method according to claim 27, wherein said at least one implantable device comprises a multiplicity of individual implantable devices, and wherein the combination of said implantable devices continuously releases dopamine agonist in vivo over a sustained period of time at a rate that results in a steady state plasma level of at least about 0.05 ng/ml for the sustained period of time.

29. A method according to claim 27, wherein said EVA comprises about 33% vinyl acetate.

30. A method according to claim 27, wherein said at least one implantable device comprises about 10 to about 85% dopamine agonist.

31. A method according to claim 27, wherein said dopamine agonist is ropinirole.

32. A method according to claim 27, wherein said dopamine agonist is pramipexole.

33. A method according to claim 27, wherein said mammal has Parkinson's disease.

34. A method according to claim 27, wherein said mammal has toxin- or disease-induced parkinsonism.

35. A method according to claim 27, wherein said mammal has a condition selected from the group consisting of erectile dysfunction and restless leg syndrome.

36. A method according to claim 27, wherein said dopamine agonist is rotigotine.

37. A method according to claim 27, wherein said dopamine agonist is selected from the group consisting of lisuride, pergolide, and bromocriptine.

38. A method according to claim 27, wherein said at least one implantable device comprises dimensions of about 2 to about 3 mm in diameter and about 2 to about 3 cm in length.

39. A method according to claim 38, wherein said at least one implantable device releases at least about 0.1 mg of dopamine agonist per day in vitro.

40. A method according to claim 27, wherein said at least one implantable device is subcutaneously implanted at a site selected from the group consisting of the upper arm, the back, and the abdomen.

41. A method according to claim 27, further comprising administration of an anti-inflammatory agent.

42. A method according to claim 41, wherein said anti-inflammatory agent is encapsulated within said matrix in said at least one implantable device.

43. A method according to claim 41, wherein said anti-inflammatory agent is encapsulated within a biocompatible, nonerodible polymeric matrix that does not comprise said dopamine agonist, and wherein said method comprises administration of said polymeric matrix comprising said anti-inflammatory agent subcutaneously.

44. A method according to claim 41, wherein said anti-inflammatory agent is administered via a route selected from the group consisting of local injection, systemic injection, subcutaneous injection, and oral administration.

45. A method according to claim 41, wherein said at least one implantable device further comprises an antioxidant.

46. A kit comprising at least one implantable device according to claim 1 and instructions for use in a method of subcutaneous administration of a dopamine agonist to a mammal in need thereof.

47. A kit according to claim 46, wherein said at least one implantable device comprises a multiplicity of individual implantable devices, and wherein when the combination of said implantable devices is implanted subcutaneously in a mammal, said implantable devices continuously release dopamine agonist in vivo over a sustained period of time at a rate that results in a steady state plasma level of at least about 0.05 ng/ml for the sustained period of time.

48. A kit according to claim 46, wherein said at least one implantable device releases dopamine agonist at a rate of at least about 0.1 mg per day in vitro.

49. A kit according to claim 46, wherein said EVA comprises about 33% vinyl acetate.

50. A kit according to claim 46, wherein said at least one implantable device comprises about 10 to about 85% dopamine agonist.

51. A kit according to claim 50, wherein said dopamine agonist is selected from the group consisting of lisuride, pergolide, and bromocriptine.

52. A kit according to claim 50, wherein said dopamine agonist is ropinirole.

53. A kit according to claim 50, wherein said dopamine agonist is pramipexole.

54. A kit according to claim 50, wherein said dopamine agonist is rotigotine.

55. An implantable device according to claim 1, wherein the steady state plasma level is about 0.01 ng/ml to about 10 ng/ml.

56. An implantable device according to claim 1, consisting essentially of the dopamine agonist, the biocompatible, nonerodible polymeric matrix, optionally an anti-inflammatory agent, and optionally an antioxidant.

57. An implantable device according to claim 15, wherein the release of the dopamine agonist results in a steady state plasma level of at least about 0.01 ng/ml for the sustained period of time.

58. An implantable device according to claim 57, wherein the steady state plasma level is about 0.01 ng/ml to about 10 ng/ml.

59. An implantable device according to claim 15, comprising dimensions of about 2 to about 3 mm is diameter and about 2 to about 3 cm in length.

60. The method according to claim 27, wherein said dopamine agonist is lisuride.

61. The method according to claim 27, wherein the steady state plasma level is about 0.01 ng/ml to about 10 ng/ml.

62. The method according to claim 27, wherein said dopamine agonist is ropinirole or rotigotine.

63. The method according to claim 27, wherein said at least one implantable device consists essentially of said dopamine agonist, said biocompatible, nonerodible polymeric matrix, optionally an anti-inflammatory agent, and optionally an antioxidant.

64. The method according to claim 27, wherein said at least one implantable device comprises about 10 to about 85% dopamine agonist, and wherein said EVA comprises about 10 to about 35% by weight vinyl acetate.

65. The method of claim 64, wherein said dopamine agonist is ropinirole.

66. The method of claim 64, wherein said dopamine agonist is lisuride.

67. The method of claim 64, wherein said dopamine agonist is pramipexole.

68. The method of claim 64, wherein said dopamine agonist is rotigotine.

69. The method according to claim 41, wherein said anti-inflammatory agent is a steroid.

70. The method according to claim 41, wherein said anti-inflammatory agent is a nonsteroidal anti-inflammatory drug ("NSAID").

71. The method according to claim 41, wherein said anti-inflammatory agent is an antihistamine.

72. A kit according to claim 46, further comprising an anti-inflammatory agent, wherein said anti-inflammatory agent is encapsulated in at least one of said at least one implantable devices.

73. A kit according to claim 46, further comprising an anti-inflammatory agent, wherein said anti-inflammatory agent is encapsulated within a biocompatible, nonerodible polymeric matrix that does not comprise said dopamine agonist.

74. A kit according to claim 46, wherein said at least one implantable device comprises dimensions of about 2 to about 3 mm in diameter and about 2 to about 3 cm in length.

75. A kit according to claim 46, wherein the steady state plasma level is about 0.01 ng/ml to about 10 ng/ml.

* * * * *